United States Patent
Heldmann et al.

(10) Patent No.: US 6,881,855 B2
(45) Date of Patent: Apr. 19, 2005

(54) NORBORNYL-SUBSTITUTED SILANES AND THE USE THEREOF

(75) Inventors: Dieter Heldmann, Munich (DE); Oliver Schaefer, Munich (DE); Juergen Stohrer, Pullach (DE)

(73) Assignee: Consortium fur Elektrochemische Industrie GmbH, Munich (DE)

(*) Notice: Subject to any disclaimer, the term of this patent is extended or adjusted under 35 U.S.C. 154(b) by 385 days.

(21) Appl. No.: 10/255,515

(22) Filed: Sep. 26, 2002

(65) Prior Publication Data

US 2003/0097015 A1 May 22, 2003

(30) Foreign Application Priority Data

Sep. 27, 2001 (DE) .......................................... 101 47 625

(51) Int. Cl.⁷ .............................. C07F 7/18; C07F 7/08; C07F 7/10; C07F 7/12
(52) U.S. Cl. ...................... 556/407; 556/411; 556/426; 556/442; 556/463; 556/428; 556/465
(58) Field of Search ................................ 556/407, 411, 556/426, 442, 428, 463, 465

(56) References Cited

U.S. PATENT DOCUMENTS 4,214,914 A * 7/1980 Ivanchev et al. ........... 106/490
4,642,356 A * 2/1987 Langner et al. ............. 549/214

FOREIGN PATENT DOCUMENTS

DE 199 19 152 C1 5/2000
DE 101 47 625 C1 10/2002

OTHER PUBLICATIONS

English Derwent Abstract AN 2000–304804 [27] Corresponding To DE 199 19 152 C1.
English Derwent Abstract AN 2002–714713 [78] Corresponding To DE 101 47 625.
Eddy, V.J. et al., Journal of Organic Chemistry, May 1987, vol. 52, No. 10, pp. 1903–1906.
Corey E.J. et al., Journal of The American Chemical Society, 1972, American Chemical Society, Washington, D.C., US, vol. 94, No. 17, pp. 6190–6191.
Lalonde G. et al., Synthersis, Sep. 1985, pp. 817–845.
English Derwent Abstract AN 2000–304804 [27] Corresponding To DE 199 19 152.
E.J. Corey, A. Venkateswarlu, Journal of the American Chemical Society 1972, 94, pp. 6190–6191.
B.M. Lalonde, T.H. Chan, Synthesis 1985, pp. 817–845.
Szabo, K. et al. Helvetica Chimica Acta 1984, 67, pp. 2128–2142.
Eddy, V.J.; Hallgren, J.E.; J. Org. Chem. 1987, 52(10), pp. 1903–1906.
Green, M.; Spencer, J.L.; Stone, F.G.A.; Tsipis, C.A.; J. Chem. Soc. Dalton Trans. 1977, pp. 1519–1525.
Magomedov, G.K.–I. et al., J. Gen. Chem. USSR (English translation) 1988, 58(1), pp. 91–93.
R. Cunico and L. Bedell, J. Org. Chem. 1980, 45, pp. 4797–4798.

* cited by examiner

*Primary Examiner*—Peter O'Sullivan
(74) *Attorney, Agent, or Firm*—Brooks Kushman P.C.

(57) ABSTRACT

Silanes of the formula $$R_a^1 R_{4-a-x} SiL_x \qquad (I)$$

where each R is identical or different and is a monovalent, optionally substituted hydrocarbon radical which is free of aliphatic carbon—carbon multiple bonds and has from 1 to 18 carbon atoms per radical,
$R^1$ is an optionally substituted 2-norbornyl radical,
L is a leaving group,
a is 1, 2 or 3 and
x is 1 or 2,
with the proviso that the sum of $a+x \leq 4$, are useful for protecting functional groups of organic compounds (2) which have at least one functional group having an active hydrogen atom, preferably as a hydroxyl group —OH, a thiol groups —SH, an amine group —NH— or —NH$_2$, a carboxyl group —COOH, or an amide group —CONH— or —CONH$_2$.

12 Claims, No Drawings

NORBORNYL-SUBSTITUTED SILANES AND THE USE THEREOF

BACKGROUND OF THE INVENTION

1. Field of the Invention

The invention relates to norbornyl-substituted silanes and the use thereof.

2. Background Art

Typical protecting group silanes such as TBM2-silane (tert-butyldimethylchlorosilane) or IPM2-silane (isopropyldimethylchlorosilane) are prepared by adding Grignard reagents to the corresponding chlorosilanes, and the remaining hydrogen is subsequently exchanged with HCl using a suitable catalyst, for example as disclosed in German patent DE-C 199 19 152:

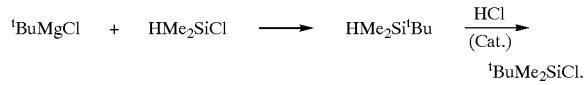

$^{t}$BuMe$_2$SiCl.

Organolithium reagents are also commonly used, for example as disclosed by E. J. Corey et al., J. AM. CHEM. SOC. 1972, 94, 6190–6191. Owing to their importance as protecting groups in organic synthesis, see, for example M. Lalonde et al., SYNTHESIS 1985, 817–845, a wide range is commercially available. However, the typical common protecting group silanes such as TBM2 and IPM2 bearing sterically demanding secondary or tertiary alkyl radicals, require expensive organometallic reagents for their preparation.

Owing to the regioselectivity of hydrosilylation, such compounds cannot be obtained directly from the corresponding alkenes, for example 2-methylprop-1-ene for TBM2 and propene for IPM2 by hydrosilylation of the latter with dimethylchlorosilane. The addition takes place preferably at the less sterically demanding carbon atom of the double bond, and so in the case of propene, leads to 1-propyl-dimethylchlorosilane and not to 2-propyl-dimethylchlorosilane, K. Szabo et al., HELV. CHIM. ACTA 1984, 67, 2128–2142.

The hydrosilylation of dimethylchlorosilane using norbornene under Pt catalysis leads preferably to exo-2-(dimethylchlorosilyl)bicyclo[2.2.1]heptane. See, e.g., V. J. Eddy et al., J. ORG. CHEM. 1987, 52(10), 1903–1906; and M. Green et al., J. CHEM. SOC. Dalton Trans. 1977, 1519–1525. This compound may also be referred to as norbornyldimethylchlorosilane (NM2-silane). Since norbornene is a disubstituted alkene, secondary alkyl radicals on silicon are thus accessible. Owing to the angle strain of norbornene, the reaction proceeds with considerably greater ease in comparison to other internal alkenes such as cyclopentene. The hydrosilylation of substituted norbornene derivatives using dimethylchlorosilane is likewise known. G. K. -I. Magomedov et al., J. GEN. CHEM. USSR (Engl. Transl.) 1988, 58(1), 91–93.

Dichlotosilanes which carry two bulky radicals such as isopropyl or tert-butyl likewise find use as protecting groups, in particular for diols (see, for example M. Lalonde, T. H. Chan, Synthesis 1985, 817–845). To prepare these compounds, organometallic reagents such as Grignard compounds are again used in a similar manner to the reaction scheme discussed previously.

Mononorbornyl-substituted dichlorosilanes are likewise known. For instance, the Pt catalyzed hydrosilylation of dichloromethylsilane using norbornene has been described which delivers the desired dichloronorbornylmethylsilane in 85% yield. M. Green et al., J. CHEM. SOC. Dalton Trans. 1977, 1519–1525).

SUMMARY OF THE INVENTION

It is an object of the invention to provide silanes which are suitable protecting group reagents for protecting functional groups of organic compounds which have at least one functional group having acidic hydrogen ("active hydrogen"), and which can be prepared inexpensively in a simple process from easily obtainable reactants. This object and other objects are achieved by the invention.

DETAILED DESCRIPTION OF THE PREFERRED EMBODIMENTS

The silanes according to the invention are used as protecting group reagents in organic synthesis where the protecting group is the silyl radical. The term "protecting group" is known to those skilled in the art of organic chemistry, for example as discussed by M. Lalonde et al., SYNTHESIS 1985, 817–845. The use as a protecting group herein accordingly refers to the reaction of a complex organic compound having at least two carbon atoms and bearing a functional group having acidic or "active" hydrogen, such as a hydroxyl, thiol, amine, amide or carboxyl group, with a norbornyl-containing silane to liberate HCl or HOSO$_2$CF$_3$ to form a corresponding silyl compound, i.e., a silyl ether, thioether, amine, amide or ester. The term "active hydrogen" means that the hydrogen of the group whose protection is desired is reactive enough to combine with the leaving group L to form a bond between the group to which the hydrogen was bonded, and the silyl protecting group. The compound protected in this manner is then subjected to one or more chemical reactions which bring about chemical or biochemical transformations on the molecular skeleton but leave the silyl protecting group untouched. These transformations ordinarily could not have been applied had the acidic hydrogen been present. After carrying out this reaction or reactions, the silyl protecting group is detached.

The invention provides the use of silanes (1) of the general formula

(I)

where each R is identical or different and is a monovalent, optionally substituted hydrocarbon radical which is free of aliphatic carbon—carbon multiple bonds and has from 1 to 18 carbon atoms per radical, R$^1$ is an optionally substituted 2-norbornyl radical, L is a chlorine atom or a radical of the formula —OSO$_2$CF$_3$, a is 1, 2 or 3 and x is 1 or 2, with the proviso that the sum of a+x≦4, which are suitable for protecting functional groups of organic compounds (2) which have at least one functional group having acidic hydrogen, preferably selected from among hydroxyl groups —OH, thiol groups —SH, amine groups —NH— and —NH$_2$, carboxyl groups —COOH, and amide groups —CONH— and —CONH$_2$, and which contain at least 2 carbon atoms.

Examples of R radicals include alkyl radicals such as the methyl, ethyl, n-propyl, isopropyl, n-butyl, isobutyl, tert-butyl, n-pentyl, isopentyl, neopentyl and tert-pentyl radicals, hexyl radicals such as the n-hexyl radical, heptyl radicals such as the n-heptyl radical, octyl radicals such as the n-octyl radical and isooctyl radicals such as the 2,2,4trimethylpentyl radical, nonyl radicals such as the n-nonyl radical, decyl radicals such as the n-decyl radical, dodecyl radicals such as the n-dodecyl radical, and octadecyl radicals such as the n-octadecyl radical; cycloalkyl radicals such as the cyclopentyl, cyclohexyl, cycloheptyl and methylcyclohexyl radicals; aryl radicals such as the phenyl, naphthyl, anthryl and phenanthryl radicals; alkaryl radicals such as the o-, m- and p-tolyl radicals, xylyl radicals and ethylphenyl radicals; and aralkyl radicals such as the benzyl radical, and the α- and β-phenylethyl radicals.

Examples of substituted R radicals include haloalkyl radicals such as the 3,3,3-trifluoro-n-propyl radical, the 2,2,2,2',2',2'-hexafluoroisopropyl radical, the heptafluoroisopropyl radical, and haloaryl radicals such as the o-, m- and p-chlorophenyl radicals. Any substituent which does not interfere with the use of the inventive compounds as protective silanes is suitable.

R is preferably an alkyl radical having from 1 to 4 carbon atoms or the phenyl radical, and is more preferably the methyl or phenyl radical.

Examples of $R^1$ radicals include those of the formula

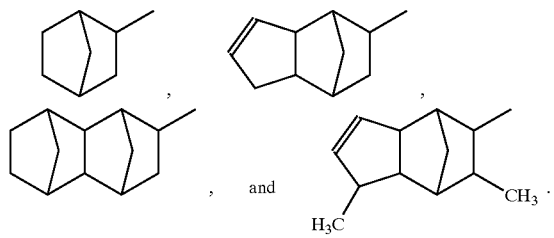

The preferred $R^1$ radical is the 2-norbornyl radical.

The L radical is a leaving group which may either be chloride $Cl^-$ or trifluoromethanesulfonate $F_3CSO_2O^-$. Trifluoromethanesulfonates are suitable in particular for silylating sterically demanding organic compounds (2).

Examples of silanes according to the invention are

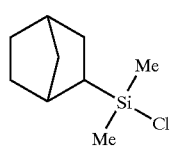

1

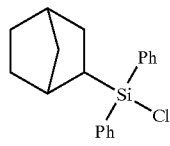

2

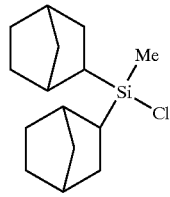

3

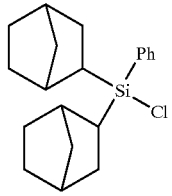

4

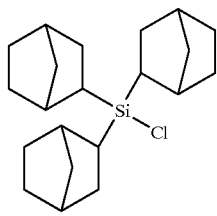

5

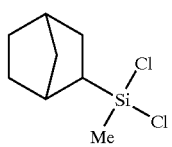

6

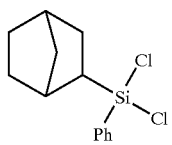

7

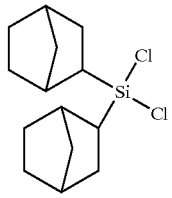

8 and also the analogous compounds where chloride (—Cl) is replaced by trifluoromethanesulfonate (—OSO$_2$CF$_3$), such as 2-norbornyldimethylsilyl trifluoromethanesulfonate and di(2-norbornyl)silyldi(trifluoromethanesulfonate).

Di(2-norbornyl)methylchlorosilane 3 is prepared by hydrosilylating norbornene using methylchlorosilane (H$_3$CSiH$_2$Cl). Tri(2-norbornyl)chlorosilane 5 is prepared by hydrosilylating norbornene using chlorosilane (H$_3$SiCl). Di(2-norbornyl)dichlorosilane 8 is prepared by hydrosilylating norbornene using dichlorosilane (H$_2$SiCl$_2$).

The trifluoromethanesulfonates are prepared by boiling the appropriate chlorides with trifluoromethanesulfonic acid. The monofunctional compounds 1 to 5 are suitable for protecting organic compounds by providing each functional group with a silyl protecting group.

The difunctional compounds 6 to 8 are suitable in particular for protecting organic compounds which have a plurality of adjacent functional groups. Examples thereof are, in particular, 1,2diols, 1,3-diols and 1,4-diols. Of course, one molecule of compounds 6 to 8 may be used to protect one functional group each of two organic compounds.

Preference is given to using the silanes (1) according to the invention as protecting groups for alcohols, carboxylic acids and amides.

Preferred functional groups which are protected by the silanes according to the invention are hydroxyl groups —OH, carboxyl groups —COOH or amide groups —CONH—, with preference is given to the hydroxyl groups. The hydroxyl groups may be of primary, secondary or tertiary alcohols. The organic compounds (2) whose functional groups are protected by the silanes according to the invention are typically complex organic compounds which are precursors to active pharmaceutical ingredients. These may be natural products or natural product analogs. In principle, these include all organic molecules which carry one of the above-cited functional groups. Organic compounds (2) are preferably compounds having from 2 to 400 carbon atoms, preferably from 3 to 100 carbon atoms, more preferably from 4 to 50 carbon atoms, and any desired constitution and configuration which may be substituted in many desired manner and whose carbon skeleton may be interrupted by heteroatoms.

In the process of the invention, the organic compounds (2) are reacted with the silanes (1). This is may be illustrated using hydroxyl group-containing organic compounds. The organic compound (2) may have one functional group, such as a hydroxyl group Z-OH, or two adjacent functional groups, such as two hydroxyl groups $Z(-OH)_2$, for example 1,2-diols, 1,3-diols or 1,4-diols. In this process, silanes (1) of general formula

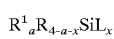  (I)

where R, $R^1$, L, a and x are each as defined above, are reacted with organic compounds (2) of general formulae Z—OH  or  (IIa)

  (IIb)

where Z is a hydrocarbon radical having from 2 to 400 carbon atoms, preferably from 3 to 100 carbon atoms, more preferably from 4 to 50 carbon atoms, which may be interrupted by one or more heteroatoms or substituted. This liberates the acid HL.

With regard to organic compounds having one functional group (IIa), preference is given to using silanes where x=1 (and a=1, 2 or 3), i.e. monofunctional silanes. This provides silylated compounds of the general formula

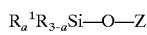  (IIIa)

As to organic compounds having two adjacent functional groups (IIb), preference is given to using silanes where x=2 (and a=1 or 2), i.e. difunctional silanes. This provides silylated compounds of the general formula

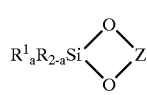  (IIIb)

However, difunctional silanes may also be used to protect one functional group, such as a hydroxyl group, in each of two organic compounds (IIa). This provides silylated compounds of the general formula

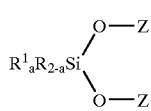  (IIIc)

The Z radical of the organic compound (2) may be any desired carbon radical which may be substituted or interrupted by heteroatoms in any desired manner. Non-limiting examples of heteroatoms are O, N, S and P. Examples of Z radicals may be the examples cited for the R radicals.

Simple model compounds were selected as examples for the process according to the invention for protecting functional groups having acidic hydrogen atoms.

Examples of such silylated compounds which should not be regarded as a restriction of the Z radical and are obtained using silanes (1) where x=1, i.e. monofunctional silanes, are:

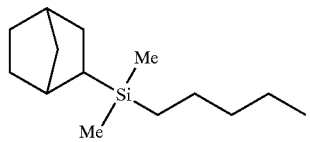

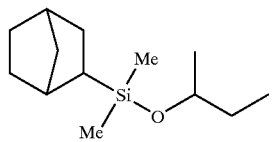

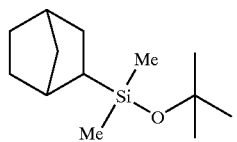

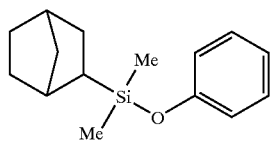

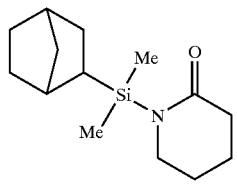

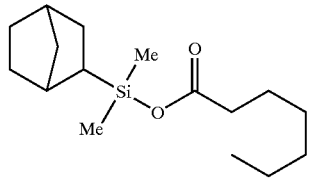

Me=methyl radical.

One example each of a protected primary, secondary, tertiary and aromatic alcohol, and also a silylated amide and a silyl ester of a carboxylic acid are shown by way of example.

An essential prerequisite for the suitability of a protecting group is that it is resistant toward a variety of reagents which would interfere with the protected functional group. To this end, stability tests, which are summarized in examples, were carried out by way of example using 2-butoxydimethyl-2-norbornylsilane in comparison to the analogous compounds 2-butoxydimethyl-tert-butylsilane and 2-butoxydimethyl-2-propylsilane disclosed by the literature. The test compound shows a very good property profile which is between those of the silanes IPM2 and TBM2. The test compound may in many cases replace these more expensive protecting groups. Since protecting groups make no contribution to the end molecule skeleton, this provides a substantial cost saving.

A further prerequisite for a protecting group is problem-free removability using suitable reagents after the reaction has been carried out. This has also been investigated and is documented in the examples.

EXAMPLE 1

Preparation of 2-norbornyldimethylchlorosilane

Norbornene (141 g, 1.50 mol) is dissolved in toluene (100 ml) and heated to 80° C. After the addition of the platinum catalyst ([COD]PtCl$_2$, 70 mg), dimethylchlorosilane (169 g, 1.8 mol) is slowly added dropwise within 60 min, and the temperature rises to 98° C. Heating is continued at 80° C. for a further 1 h. Excess silane, unconverted norbornene and the solvent are distilled off at atmospheric pressure. The residue is fractionally distilled using a membrane pump vacuum. 255 g (93%) of a colorless liquid having b.p. of 120° C./10 mbar are obtained. Purity 99.7% (assessed by GC (gas chromatography)).

$^1$H NMR (CDCl$_3$): 0.15 (s, 3H), 0.25 (s, 3H); 0.6 (t, 1H); 0.9–1.1 (m, 4H), 1.2–1.4 (m, 4H), 2.1 (2 s, overlapping, 2H). The exo/endo ratio is 93:7 (GC). The analytical data reported always relate to the main isomer.

EXAMPLE 2

Preparation of di(2-norbornyl)dichlorosilane

Dichlorosilane (18.5 g, 0.18 mol) is condensed into a cold trap at −78° C. and dissolved in precooled xylene (200 ml). The temperature is −10° C. after the addition. First norbornene (34.5 g, 0.37 mol) and then the catalyst [COD]PtCl$_2$ (1% solution in in CH$_2$Cl$_2$, 2.50 ml) are added, whereupon an exothermic reaction starts spontaneously. The temperature rises to 46° C. and an ice bath is used to reduce the temperature to 40° C. After 15 min, the temperature begins to fall again. According to GC (gas chromatography), about 50% of the norbornene is consumed. The reaction mixture is heated to 80° C. for 15 min, then held at 40° C. for a further 1.5 h. The conversion of the norbornene according to GC is >90%. The reaction mixture is fractionally distilled. The main fraction at b.p. 118° C./1 mbar consists of 49.8 g of dichlorodinorbornylsilane. Yield 94%. Purity 95.7% (GC).

$^1$H NMR (CDCl$_3$): 1.0 (t, 2H), 1.1–1.25 (m, 6H), 1.35–1.45 (m, 4H), 1.45–1.55 (m, 4H), 1.55–1.65 (m, 2H), 2.25 (s, 2H), 2.35 (s, 2H).

EXAMPLE 3

General Method for Preparing 2-norbornyldimethylsilyl Ethers

The alcohol to be silylated (50 mmol), as per Table 1, and imidazole (110 mmol) are dissolved in anhydrous DMF (50 ml). Dimethylnorbornylchlorosilane (55 mmol), whose preparation is described in Example 1, is added dropwise. The addition is exothermic with primary and secondary alcohols, and generally requires heating to 80° C. for tertiary alcohols. After complete reaction (GC analysis), the reaction mixture is poured into water (50 ml) and extracted using pentane (3×150 ml). The combined organic phases are washed with water and saturated NaCl solution (100 ml each), dried over Na$_2$SO$_4$ and concentrated on a rotary evaporator. The crude yields are virtually quantitative. The residue is fractionally distilled under reduced pressure in order to achieve very high purity (>95%). The results are summarized in Table 1.

TABLE 1

| Alcohol | Product | b.p.[° C.] (1 mbar) | Purity (GC, area %) | $^1$H NMR (CDCl$_3$) |
| --- | --- | --- | --- | --- |
| 1-Butanol | 1-Butoxydimethyl-norbornylsilane | 63–64 | 96.0 | 0.0, 0.1(2s, 6H), 0.6 (t, 1H), 0.9(t, 3H), 1.1–1.5(m, 12H), 2.2 (s, 2H), 3.6(t, 2H) |
| 2-Butanol | 2-Butoxydimethyl-norbornylsilane | 68 | 98.5 | 0.05(2s, 6H), 0.1(d, 1H), 0.6(t, 1H), 0.85 (t, 3H), 1.1(d, 4H), 1.15–1.25(m, 4H), 1.3–1.45(m, 4H), 1.5(d, 2H), 2.2(s, 2H), 3.65 (q, 1H) |
| tert-Butanol | tert-Butoxydimethyl-norbornylsilane | 88–90 (10 mbar) | — | 0.1, 0.15(2s, 6H), 0.4–0.55(m, 1H), 0.95–1.6 (m, 8H), 1.2(s, 9H), 2.2(2s, 2H) |
| Cyclohexanol | Cyclohexoxy-dimethylnorbornyl-silane | 85–87 | 98.0 | 0.15–0.2(m, 6H), 0.6 (t, 1H), 1.1–1.5(m, 14H), 1.6–1.8(t, 4H), 2.2(s, 2H), 3.5–3.6 (m, 1H) |
| Phenol | Phenoxydimethyl-norbornylsilane | 100 | 98.0 | 0.1(2s, 6H), 0.7(t, 1H), 1.1–1.3(m, 5H), 1.3–1.5(m, 3H), 2.2(d, 2H), 6.7–7.1(m, 5H) |

EXAMPLE 4

Preparation of 2-norbornyldimethylsilyl Trifluoromethanesulfonate

At room temperature, trifluoromethanesulfonic acid (7.50 g, 49.0 mmol) is added dropwise to 2-norbornyldimethylchlorosilane (9.50 g, 49.3 mmol), whose preparation is described in Example 1. The reaction mixture is heated to 60° C. for 10 h. The crude product is distilled under oil pump vacuum. 12.3 g (83%) of colorless, moisture-sensitive liquid having b.p. 100–105° C. (1 mbar) is obtained. Purity 93% (GC).

$^1$H NMR (CDCl$_3$): 0.4 (2s, 6H), 0.9 (t, 1H), 1.1–1.4 (m, 4H), 1.5 (d, 2H), 1.6 (d, 2H), 2.3 (s, 2H).

EXAMPLE 5

Preparation of di(2-norbornyl)silyldi (trifluoromethanesulfonate)

The procedure of Example 4 is repeated, except that instead of 2-norbornyldimethylchlorosilane, di(2-norbornyl)dichlorosilane, whose preparation is described in Example 2, is used.

EXAMPLE 6

Preparation of Silylated Tert-Butanol Using 2-norbornyldimethylsilyl-trifluoromethanesulfonate 2-Norbornyldimethylsilyltrifluoromethanesulfonate (4.54 g, 15 mmol), whose preparation is described in Example 4, is added at room temperature to a solution of tert-butanol (0.74 g, 10.0 mmol) and 2,6-lutidine (2.24 g, 19.6 mmol). The reaction commences immediately and exothermically at room temperature. After 2 h, the mixture is washed with 1M HCl, distilled H$_2$O and saturated NaCl solution (10 ml each), the solvent is taken off on a rotary evaporator and the residue distilled under reduced pressure. The product is identical to that described in Example 3.

EXAMPLE 7

Preparation of Silylated Heptanoic Acid

Heptanoic acid (6.51 g, 49.5 mmol) and dimethylnorbornylchlorosilane (9.82 g, 51.0 mmol), whose preparation is described in Example 1, are dissolved in CH$_2$Cl$_2$ (10 ml, dry). With stirring, imidazole (6.94 g, 101 mmol) is added, and an exothermic reaction begins. The mixture is stirred at room temperature overnight, then poured into 100 ml of H$_2$O and extracted using pentane (3×100 ml). The combined organic phases are washed with saturated NaHCO$_3$ solution (100 ml) and dried over Na$_2$SO$_4$, the solvent taken off on a rotary evaporator and the residue (12.7 g) distilled under reduced pressure. Yield 6.0 g (42%) of colorless liquid, purity 96% (GC), $^1$H NMR (CDCl$_3$): 0.1 (2s, 6H), 0.7–0.9 (m, 4H), 1.0–1.6 (m, 16H), 2.2 (m, 4H).

EXAMPLE 8

Preparation of Silylated 2-pyrrolidone

2-Pyrrolidone (4.26 g, 49.6 mmol), dimethylnorbornylchlorosilane (9.44 g, 49.0 mmol), whose preparation is described in Example 1, and 4-dimethylaminopyridine (0.62 g, 5.00 mmol) are dissolved in abs. CH$_2$Cl$_2$ (20 ml). NEt$_3$ (triethylamine) (5.06 g, 49.5 mmol) is cautiously added dropwise (exothermic reaction). The batch is diluted using further CH$_2$Cl$_2$ (10 ml) and stirred overnight. The mixture is poured into H$_2$O (100 ml) and extracted using pentane (3×100 ml). The combined organic phases are washed with saturated NaHCO$_3$ solution (100 ml), dried over Na$_2$SO$_4$ and concentrated on a rotary evaporator. The silylated amide is obtained as a colorless oil (9.8 g, 83%).

$^1$H NMR (CDCl$_3$): 0.2 (2s, 6H), 1.0 (t, 1H), 1.1 (s, 2H), 1.15 (t, 2H), 1.2 (t, 2H), 1.4 (dd, 4H), 2.0–2.1 (m, 2H), 22.2–2.4 (m, 4H), 3.4 (t, 2H).

EXAMPLE 9

Cleavage of Silylated 1-butanol

The hydrolysis kinetics are recorded in a manner similar to that disclosed by R. F. Cunico et al., J. ORG. CHEM. 1980, 45, 4797–4798 using 0.1% ethanolic HCl. The samples are analyzed by GC (gas chromatography) after the stated time intervals. The percentage decrease in the silyl ether quantity is determined by comparison of areas. Abbreviations:

M3: 1-Butoxytrimethylsilane
IPM2: 1-Butoxydimethylisopropylsilane
M2N: 1-Butoxydimethylnorbornylsilane
TBM2: 1-Butoxytert-butyldimethylsilane

TABLE 2

| T [min] | M3 | IPM2 | M2N | TBM2 |
|---|---|---|---|---|
| 0 | 97 | | | |
| 2 | 3 | | | |
| 33 | 2 | | | |
| 0 | | 92 | | |
| 2 | | 73 | | |
| 9 | | 37 | | |
| 16 | | 18 | | |
| 23 | | 11 | | |
| 32 | | 9 | | |
| 0 | | | 96 | |
| 2 | | | 92 | |
| 24 | | | 76 | |
| 53 | | | 63 | |
| 76 | | | 56 | |
| 176 | | | 37 | |
| 471 | | | 21 | |
| 534 | | | 19 | |
| 0 | | | | 96 |
| 2 | | | | 85 |
| 42 | | | | 79 |
| 241 | | | | 54 |
| 557 | | | | 28 |

EXAMPLE 10

Stability Test

To test stability against reagents, two samples each of 2-butoxydimethylnorbornylsilane are dissolved in a suitable solvent and one sample admixed with a reagent as per Table 3. After a suitable time, the sample and the blank sample are worked up in an identical manner and analyzed by GC (gas chromatography). The stability is determined from the area comparison. The results are summarized in Table 3. "Stable" refers to a percentage area of >90% and "unstable" to a percentage area of <10%. All tests were, unless otherwise stated, carried out at room temperature.

TABLE 3

| Reagent | T | Silyl ether |
|---|---|---|
| BuMgCl in THF | after 18 h | stable |
| 0.05 N NaOH in MeOH | after 12 min | stable |
| 0.05 N NaOH in MeOH | after 1 h | stable |
| KF in MeOH | after 1 h | stable |
| KF in MeOH | after 7 h at 65° C. | unstable |
| nBu$_4$NF in THF | after 5 min | unstable |
| LiAlH$_4$ in THF | after 1 h | stable |
| LiAlH$_4$ in THF | after 16 h | stable |
| nBuLi in hexane + THF | after 1 h | stable |
| nBuLi in hexane + THF | after 16 h | stable |

Table 3 clearly shows that the protecting group is stable toward a variety of organometallic reagents, but can easily be cleaved by fluoride ions or acid.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention. The terms "a" and "an" mean "one or more than one" unless indicated otherwise.

What is claimed is:

1. A process of protecting a functional group of an organic compound containing minimally two carbon atoms, said functional group containing an active hydrogen, said process comprising reacting said functional group with a silane (1) of the formula $$R_a^1R_{4-a-x}SiL_x \qquad (I)$$

where each R is identical or different and is a monovalent, optionally substituted C$_{1-18}$ hydrocarbon radical free of aliphatic carbon—carbon multiple bonds, R$^1$ is an optionally substituted 2-norbornyl radical, L is a chlorine atom or a radical of the formula —OSO$_2$CF$_3$, a is 1, 2 or 3 and x is 1 or 2, with the proviso that the sum of a+x≦4.

2. The process of claim 1, wherein the functional group containing an active hydrogen is selected from the group consisting of hydroxyl groups —OH, thiol groups —SH, amine groups —NH— and —NH$_2$, carboxyl groups —COOH, and amide groups —CONH— and —CONH$_2$.

3. The process of claim 1, wherein the functional group containing active hydrogen is selected from the group consisting of hydroxyl groups —OH, carboxyl groups —COOH, and amide groups —CONH—.

4. The process of claim 1, wherein the functional groups containing active hydrogen are hydroxyl groups —OH of primary, secondary or tertiary alcohols or of 1,2-diols, 1,3-diols or 1,4-diols.

5. The process of claim 1, wherein the silane (1) used is 2-norbornyldimethylchlorosilane.

6. A protecting agent suitable for use in the process of claim 1, said protecting agent having the formula $$R_2^1R_{1-b}SiL_{1+b}$$

or the formula $$R_1^3SiL,$$

wherein R is a monovalent, optimally substituted C$_{1-18}$ hydrocarbon radical free of ethylene unsaturation;

R$^1$ is an optionally substituted 2-norbornyl radical,

L is a chlorine atom or a radical of the formula —OSO$_2$CF$_3$, and b is 0 or 1.

7. The protecting agent of claim 6, selected from the group consisting of di(2-norbornyl)methylchlorosilane, tri(2-norbornyl)chlorosilane, di(2-norbornyl)dichlorosilane, and di(2-norbornyl)silyldi(trifluoromethanesulfonate).

8. The protecting agent of claim 6 which is di(2-norbornyl)methylchlorosilane.

9. The protecting agent of claim 6 which is tri(2-norbornyl)chlorosilane.

10. The protecting agent of claim 6 which is di(2-norbornyl)dichlorosilane.

11. The protecting agent of claim 6 which is di(2-norbornyl)silyl di(trifluoromethanesulfonate).

12. A protecting agent suitable for use in the process of claim 1, comprising 2-norbornyldimethylsilyltrifluoromethanesulfonate.

* * * * *